(12) United States Patent
Kim et al.

(10) Patent No.: US 12,168,020 B2
(45) Date of Patent: Dec. 17, 2024

(54) METHOD FOR AMELIORATING, PREVENTING OR TREATING MUSCULAR ATROPHY OR SARCOPENIA BY ADMINISTERING COMPOSITION COMPRISING 2'-FUCOSYLLACTOSE AS ACTIVE INGREDIENT

(71) Applicant: ADVANCED PROTEIN TECHNOLOGIES CORP., Suwon-si (KR)

(72) Inventors: Yeon Ji Kim, Daegu (KR); Kyung Ho Kim, Daegu (KR); Chul Soo Shin, Suwon-si (KR); Jong Won Yoon, Seongnam-si (KR); Seon Min Jeon, Daegu (KR); Young Ha Song, Yongin-si (KR); Jong Gil Yoo, Suwon-si (KR); Ji Eun Kim, Hwaseong-si (KR)

(73) Assignee: ADVANCED PROTEIN TECHNOLOGIES CORP., Suwon-si (KR)

( * ) Notice: Subject to any disclaimer, the term of this patent is extended or adjusted under 35 U.S.C. 154(b) by 0 days.

(21) Appl. No.: 17/896,339

(22) Filed: Aug. 26, 2022

(65) Prior Publication Data
US 2023/0158052 A1 May 25, 2023

Related U.S. Application Data

(63) Continuation of application No. PCT/KR2021/018900, filed on Dec. 13, 2021.

(30) Foreign Application Priority Data

Nov. 23, 2021 (KR) ................ 10-2021-0162483

(51) Int. Cl.
*A61K 31/702* (2006.01)
*A61P 21/06* (2006.01)

(52) U.S. Cl.
CPC ............ *A61K 31/702* (2013.01); *A61P 21/06* (2018.01)

(58) Field of Classification Search
CPC .................................................. A61K 31/702
See application file for complete search history.

(56) References Cited

U.S. PATENT DOCUMENTS

2022/0273016 A1* 9/2022 Barile .................. A23L 33/125

FOREIGN PATENT DOCUMENTS

| KR | 10-2018-0102431 A | 9/2018 |
|---|---|---|
| KR | 10-1921085 B1 | 11/2018 |
| KR | 10-2019-0045079 A | 5/2019 |
| KR | 10-2019-0130720 A | 11/2019 |
| KR | 10-2020-0033544 A | 3/2020 |
| KR | 10-2020-0033546 A | 3/2020 |
| KR | 10-2020-0097751 A | 8/2020 |
| KR | 10-2021-0013007 A | 2/2021 |
| KR | 10-2021-0042039 A | 4/2021 |
| KR | 10-2021-0116783 A | 9/2021 |
| WO | 2016/029113 A1 | 2/2016 |
| WO | 2020/174386 A1 | 9/2020 |
| WO | 2021/011905 A1 | 1/2021 |
| WO | 2021/048440 A1 | 3/2021 |
| WO | 2022/115347 A1 | 6/2022 |

OTHER PUBLICATIONS

Cruz-Jentoft et al., Age and Ageing, "Sarcopenia: European consensus on definition and diagnosis", 2010, vol. 39, pp. 412-423 (Year: 2010).*
Skura, C.L. et al., Neurology, "Albuterol increases lean body mass in ambulatory boys with Duchenne or Becker muscular dystrophy", 2008, vol. 70, pp. 137-143 (Year: 2008).*
Csete, M., Geriatric Anesthesia, "Basic Science of Frailty-Biological Mechanisms of Age-Related Sarcopenia", Feb. 2021, vol. 132, No. 2, pp. 293-304 (Year: 2021).*
Li, W., Biomedicine & Pharmacotherapy, 2020, vol. 131, pp. 110721, 7 pages (Year: 2020).*
Rudolf, R. et al., Frontiers in Aging Neuroscience, May 2014, vol. 6, 11 pages (Year: 2014).*
Ogden, C. et al., Advance Data From Vital and Health Statistics, 2004, vol. 347, 18 pages (Year: 2004).*
International Search Report of PCT/KR2021/018900 dated Aug. 17, 2022 [PCT/ISA/210].
Extended European Search Report issued Jul. 29, 2024 in European Application No. 21953623.2.

* cited by examiner

*Primary Examiner* — Bahar Craigo
(74) *Attorney, Agent, or Firm* — Sughrue Mion, PLLC

(57) ABSTRACT

Disclosed is a method for preventing or treating muscular atrophy or sarcopenia, the method comprising administering a composition comprising 2'-fucosyllactose (2'-FL) as an active ingredient to a subject in need thereof. The composition administered to the subject increases the expression of genes related to mitochondrial function enhancement and mitochondrial biosynthesis, and reduces the expression of atrogin-1 and MuRF1 genes, which are markers for muscular atrophy, thereby providing effects of strengthening muscles and preventing muscular atrophy or sarcopenia.

10 Claims, 11 Drawing Sheets

A

B

METHOD FOR AMELIORATING, PREVENTING OR TREATING MUSCULAR ATROPHY OR SARCOPENIA BY ADMINISTERING COMPOSITION COMPRISING 2'-FUCOSYLLACTOSE AS ACTIVE INGREDIENT

CROSS-REFERENCE TO RELATED APPLICATIONS

This application is a Bypass Continuation of PCT International Application No. PCT/KR2021/018900, filed on Dec. 13, 2021, which is based on and claims priority to Korean Patent Application No. 10-2021-0162483, filed on Nov. 23, 2021, the disclosures of which are incorporated herein by reference in their entireties.

BACKGROUND OF THE INVENTION

Field of the Invention

The present invention relates to a method for ameliorating, preventing or treating muscular atrophy or sarcopenia, the method comprising administering a composition comprising 2'-fucosyllactose (2'-FL) as an active ingredient to a subject in need thereof.

Description of the Related Art

Muscles account for more than 50% of body weight on average and function to support and move the body along with bones and ligaments. Therefore, damage to the muscles responsible for body movement causes discomfort in movement in the short term, and reduces quality of life and increases medical and social expenses in the long term. In general, muscular atrophy or sarcopenia refers to a condition characterized by decreased physical function and vulnerability to stimulation caused by reduced muscle mass and weakness. Muscular atrophy or sarcopenia is classified into primary muscular atrophy or sarcopenia due to aging-related factors such as lack of mechanical stimulation, for example, lack of physical activity, aging of astrocytes, a type of stem cells, decreased activity of neuromuscular junctions, decreased mitochondrial function, and nutritional deficiency including insufficient protein intake, and secondary muscular atrophy or sarcopenia caused by denervation due to stroke including muscle disorders (e.g., muscle damage, muscle (motor) nerve damage, degenerative central nervous system diseases, spinal diseases, genetic diseases, etc.), various chronic diseases (e.g., cancer cachexia, AIDS, chronic heart failure, chronic obstructive pulmonary disease (COPD), sepsis, etc.), excessive use of drugs (e.g., corticoid-based steroids, statin-based hyperlipidemia drugs, antibiotic penicillin-based penicillamine, etc.), changes in endocrine system hormones (e.g., growth hormones, thyroid hormones, adrenal hormones, vitamin D, etc.) and changes in sex hormones (testosterone, estrogen, etc.), and proinflammatory cytokine imbalance.

In an aging society, it is important that muscular atrophy or sarcopenia not be predicted or diagnosed merely based on reduction in muscle mass. There are various causes of muscular atrophy or sarcopenia. However, muscular atrophy causes reduction in the cross-sectional area of muscle fibers, protein amounts and muscle strength, and increases in fatigue and insulin resistance, thus increasing the incidence and mortality of other diseases. Therefore, clinical diagnosis through various measurements is very important.

In general, muscle mass peaks in the 20s and 30s, and then gradually decreases by 8% every 10 years from the age of 40 to the age of 70, and decreases by about 10% every 10 years after the age of 70. In particular, the decrease in muscle mass in the lower extremities is more pronounced than that in the upper extremities. Therefore, the prevalence of sarcopenia is more than 10% in people 65 years of age or older and increases by up to 50% or more after the age of 80. Although the diagnostic criteria for geriatric sarcopenia differ by country, the common criteria are physical activity ability such as muscle mass, grip strength, and walking speed. This muscle loss is caused by decrease in metabolic ability and physical activity due to aging, hormonal imbalance, increase in reactive oxygen species, nutritional deficiency, inflammation, or various degenerative diseases. Sarcopenia is not only a health problem in itself, but also a risk factor that can cause other diseases or health problems. When both muscle action and the load applied to the muscles are reduced due to decreased physical activity, contractile protein synthesis decreases and proteolysis increases, resulting in further restriction in physical activity due to reduced grip strength, walking speed, and standing balance, and increases in the risk of osteoporosis, falls, and fractures, thus causing inability to be physically active.

In particular, as life expectancy increases due to medical care, nutritional status, and environmental improvement, the elderly population is rapidly increasing all over the world and thus muscular atrophy or sarcopenia due to aging is on the rise. In addition, patients with hereditary muscular atrophy such as Duchenne muscular atrophy and Becker muscular atrophy account for about 4 per 100,000 population, and it is estimated that the number of patients with muscular atrophy or sarcopenia is quite high if patients with other muscular atrophy such as Lou Gehrig's disease or Kennedy's disease are included.

As the global population with muscular atrophy or sarcopenia increases, in November 2016, the US Centers for Disease Control and Prevention assigned the disease code (M62.84) to sarcopenia for the first time in the world and classified sarcopenia as a disease. Sarcopenia was officially registered in the 10th revision of the Statistical Classification of Diseases and a disease code was also assigned to sarcopenia in Japan in 2018. A sarcopenia disease code was assigned to the revised edition of the Korean statistical classification of diseases in Korea in 2021, and a sarcopenia diagnosis code will be included in the $8^{th}$ revision of the Korean Standard Classification of Diseases.

Although muscular atrophy or sarcopenia is largely related to aging, adolescents and young adults are also not free from sarcopenia due to convenient living environment, sedentary lifestyle, lack of exercise, and nutritional imbalance of modern people. Recently, in addition to exercise that contributes to the improvement of muscle growth and muscle strength, various supplements such as proteins and related ingredients necessary for muscle growth are commercially available. Excessive intake of protein supplements beyond necessary causes a continuous burden on the kidneys oxides generated during protein metabolism are discharged through the kidneys, thus continuously putting a strain on the kidneys, and it can adversely affect health of people having weak or poor kidney function, and the elderly having poor metabolic ability.

Zolgensma®, which is a gene therapy medicine for spinal muscular atrophy (SMA), is the world's only therapeutic agent for muscular dystrophy and is known to be a gene therapy medicine that is capable of treating SMA through single administration. However, other therapeutic agent for muscular dystrophy is under development or has not been developed to date. Although there is no therapeutic agent product for sarcopenia developed to date, the size of the market for therapeutic agents for sarcopenia is expected to be over $11 billion (about 12.5 trillion KRW) in consideration of the increasing trend of the global population with muscular atrophy or sarcopenia. The health functional food market is also growing rapidly. A variety of market reports showed that the market for therapeutic agents for sarcopenia is expected to grow larger than the market for therapeutic agents for osteoporosis, which is worth about 20 trillion won a year in the United States alone.

Therefore, there is a need to develop a novel material capable of preventing, ameliorating or treating muscular atrophy or sarcopenia, which has a mechanism capable of fundamentally promoting synthesis of muscle proteins and inhibiting degradation of muscle proteins while minimizing side effects.

SUMMARY OF THE INVENTION

Therefore, the present invention has been made in view of the above problems, and it is an object of the present invention to provide a novel method for preventing or treating muscular atrophy or sarcopenia, the method comprising administering a composition comprising 2'-fucosyllactose (2'-FL) as an active ingredient to a subject in need thereof.

In accordance with the present invention, the above and other objects can be accomplished by the provision of a pharmaceutical composition for preventing or treating muscular atrophy containing 2'-fucosyllactose (2'-FL) as an active ingredient.

The muscular atrophy may be, for example, any one selected from primary muscular atrophy and secondary muscular atrophy. In this case, the primary muscular atrophy, for example, may be induced by any one selected from a lack of mechanical stimulation, aging of astrocytes, decreased activity of neuromuscular junctions, decreased mitochondrial function, and nutritional deficiency. In addition, the secondary muscular atrophy may be, for example, induced by any one selected from denervation due to stroke, chronic diseases, excessive drug use, changes in endocrine system hormones and sex hormones, and imbalance of proinflammatory cytokines.

In accordance with another aspect of the present invention, provided is a pharmaceutical composition for preventing or treating sarcopenia containing 2'-fucosyllactose (2'-FL) as an active ingredient.

The sarcopenia may be, for example, any one selected from primary sarcopenia and secondary sarcopenia. In this case, the primary sarcopenia, for example, may be induced by any one selected from a lack of mechanical stimulation, aging of astrocytes, decreased activity of neuromuscular junctions, decreased mitochondrial function, and nutritional deficiency. In addition, the secondary sarcopenia may be, for example, induced by any one selected from denervation due to stroke, chronic diseases, excessive drug use, changes in endocrine system hormones and sex hormones, and imbalance of proinflammatory cytokines.

In accordance with another aspect of the present invention, provided is a food composition for ameliorating muscular atrophy containing 2'-fucosyllactose (2'-FL) as an active ingredient. In accordance with another aspect of the present invention, provided is a food composition for ameliorating sarcopenia containing 2'-fucosyllactose (2'-FL) as an active ingredient. In accordance with another aspect of the present invention, provided is a food composition for strengthening muscles containing 2'-fucosyllactose (2'-FL) as an active ingredient.

BRIEF DESCRIPTION OF THE DRAWINGS

The above and other objects, features, and other advantages of the present invention will be more clearly understood from the following detailed description taken in conjunction with the accompanying drawings, in which.

DETAILED DESCRIPTION OF THE INVENTION

Figure 1:
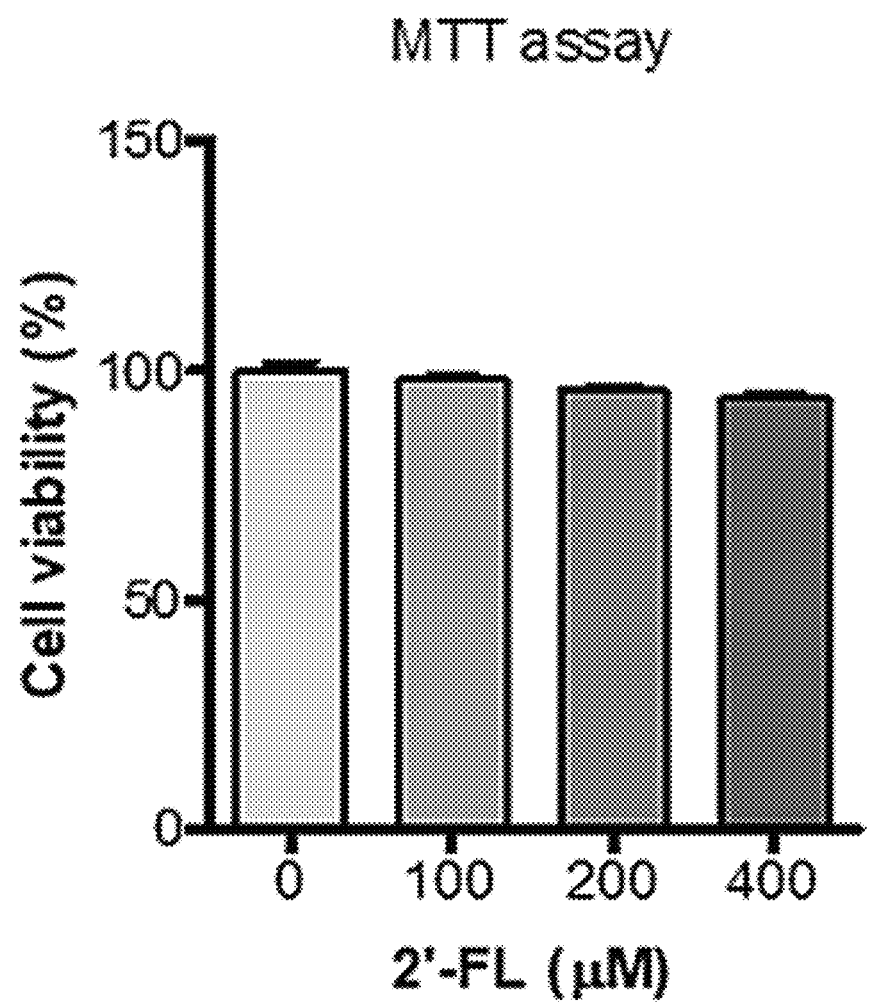
FIG. 1 shows cell viability upon treatment with 2'-FL.

In one embodiment of the present invention, it was found that 2'-FL facilitates the differentiation of C2C12 myoblasts into myotubes, increases mtDNA expression and mitochondrial density, and increases expression of PGC-1α and NRF2 mRNA, which are genes related to mitochondrial biosynthesis, and thereby improves mitochondrial functions.

Also, in one embodiment of the present invention, it was found that 2'-FL has effects of preventing reduction in the number of muscle cells and mitochondrial functions caused by treatment with dexamethasone, a synthetic ingredient of glucocorticoid among steroid hormones, and of reducing expression of genes of atrogin-1 and MuRF1, which are markers for muscular atrophy. As a result, it was also found that 2'-FL has effects of strengthening muscles and of ameliorating, preventing or treating muscular atrophy or sarcopenia.

Therefore, the present invention provides a method for preventing or treating muscular atrophy or sarcopenia, the method comprising administering a composition comprising 2'-fucosyllactose (2'-FL) as an active ingredient to a subject in need thereof.

The muscular atrophy or sarcopenia may be, for example, any one selected from primary muscular atrophy or sarcopenia and secondary muscular atrophy or sarcopenia.

In this case, the primary muscular atrophy or sarcopenia may be, for example, induced by any one selected from a lack of mechanical stimulation (including a lack of physical activity), aging of astrocytes which are stem cells, decreased activity of neuromuscular junctions, decreased mitochondrial functions, and nutritional deficiency (including insufficient protein intake), but is not limited thereto.

In addition, the secondary or muscular atrophy sarcopenia may be, for example, induced by any one selected from denervation due to stroke (including muscle diseases such as muscle damage, muscle (motor) nerve damage, degenerative central nervous system diseases, spinal diseases, and genetic diseases), chronic diseases (including cancer cachexia, AIDS, chronic heart failure, chronic obstructive pulmonary diseases (COPD), sepsis, and the like), excessive use of drugs (including corticosteroids, statin-based drugs for hyperlipidemia, or antibiotic penicillin-based therapeutic agents for rheumatism, and the like), changes in endocrine system hormones and sex hormones (including growth hormones, thyroid hormones, adrenal hormones, vitamin D, testosterone, estrogen, and the like), and imbalance of proinflammatory cytokines, but is not limited thereto.

Active research on aging and sarcopenia has elucidated the functions of genes and related proteins involved in reduction in muscle mass and number of muscle cells, and myocyte degeneration of aged muscles. Sarcopenia has been defined as the starting point of a condition in which the metabolic ability of body organs decreases due to aging, and disorders occur or the risk of death increases when exposed to physical and mental stress. Ameliorating sarcopenia is the key to preventing aging-related senescence.

Nutrients or nutritional factors that directly affect muscle mass and strength include proteins, vitamin D, various antioxidants, and omega-3 fatty acids. Protein deficiency causes decreased muscle synthesis and directly results in muscle loss. Vitamin D, omega-3 fatty acids and antioxidants are known to prevent or ameliorate sarcopenia through immunity and anti-inflammatory activity.

Reduced physical activity causes reduced muscle action, and decreased load on muscles, resulting in decreased muscle contraction-related protein synthesis and increased muscle protein decomposition. As a result, physical activity becomes more difficult due to reduction in grip strength, walking speed, and standing balance.

Meanwhile, the types of diseases that can be prevented or treated by the pharmaceutical composition of the present invention will be described in more detail below.

The mechanism of occurrence of sarcopenia includes the aging of astrocytes, a type of stem cells that produce muscle, degenerative central nervous diseases, loss of motor nerves and weakness of motor nerve function, decreased activity of neuromuscular junctions, and changes in endocrine system hormones (growth hormones, thyroid gland hormones, adrenal hormones, and the like), increased inflammatory cytokines, decreased mitochondrial function, decreased food intake (decreased intake of proteins and related nutrients), decreased activity, weak teeth, excessive drinking, insufficient sleep time and the like.

Chronic diseases (cancer cachexia, AIDS, chronic heart failure, chronic obstructive pulmonary diseases (COPD), sepsis, and the like) also cause muscular atrophy or sarcopenia. Cancer cachexia is a multifactorial disease characterized by weight loss caused by metabolic disorders and loss of appetite during progression of cancer. In clinical practice, cancer cachexia reduces the effectiveness of chemotherapy and increases mortality, so it is handled along with chemotherapy. Cachexia is accompanied by systemic weakness and muscle fatigue through muscular atrophy, and causes decline in lung muscles, respiratory failure and thus increased mortality. In cachexia, anorexia caused by cancer suppresses protein synthesis and inflammatory cytokines promote protein degradation, thereby inducing muscular atrophy.

AIDS causes muscular atrophy along with excessive protein degradation due to abnormal cytokine production, nutritional abnormalities, and endocrine system hormone abnormalities. Unlike other diseases, AIDS patients have an about 10 to 35% higher resting energy consumption than normal patients, and AIDS infection affects the pituitary hormone and facilitates the secretion of cortisol, which is a stress hormone, to promote muscle protein breakdown and inhibit protein synthesis, thereby causing muscular atrophy.

Chronic heart failure is characterized by great decline in exercise ability and activity ability in daily life due to respiratory difficulties and increased fatigue. Patients with chronic heart failure undergo muscular atrophy as the ubiquitin proteasome, autophagy, and myocyte death increase due to increased inflammatory cytokines, decreased protein synthesis, growth hormone resistance, and hyperactivity of the renin-angiotensin-aldosterone system.

Chronic obstructive pulmonary disease (COPD) is a progressive lung disease caused by excessive inflammation resulting from severe damage to the airways and lungs. Symptoms thereof include emphysema due to lung tissue destruction, chronic bronchitis, cough, and shortness of breath. About 40% of COPD patients show muscular atrophy characterized by reduced muscle mass and muscle function and gradually consume muscles, resulting in loss of exercise capacity and increased mortality.

Muscular atrophy or sarcopenia may also be caused by steroid abuse, or statin-based therapeutic agents for hyperlipidemia, or antibiotic penicillin-based therapeutic agents for rheumatoid arthritis. When steroids are used for a long time for the treatment of muscle inflammatory diseases such as dermatomyositis, they are beneficial in relieving inflammation, but result in muscular atrophy. When hyperlipidemic patients having no history of muscle disease are administered with statins, they may undergo muscular atrophy along with subacute muscle pain, fatigue, muscle weakness, myoglobinuria, and creatine kinase (CK) elevation. Statins lower the level of ubiquinone (CoQ10), which is highly responsible for mitochondrial cellular respiration and antioxidant functions, increase muscle protein degradation through the ubiquitin proteasome pathway (UPP), and affect mitochondrial death and apoptosis, decreased mitochondrial calcium regulation function, and increased reactive oxygen species, thus causing muscle loss. Among drugs, penicillamine-based penicillin is mainly used for rheumatoid arthritis, which is known to cause inflammatory muscular atrophy.

Myasthenia gravis is an autoimmune disease, characterized by drooping eyelids, double vision, and whole body weakness due to the failure in the transmission of nerve impulses to the muscles. In the initial stage, it is merely regarded as a simple symptom such as fatigue or aging. However, severe symptoms may result in respiratory muscle paralysis.

Spinal muscular atrophy (SMA), which is caused by damage to the nerves that control muscles, is an example of a neurodegenerative disease. SMA is an autosomal recessive genetic disease caused by mutations in the SMN1 gene encoding the survival motor neuron (SMN) proteins in eukaryotes. Spinal muscular atrophy refers to a group of clinically and genetically diverse diseases characterized by symmetrical muscle weakness or loss due to degeneration or loss of anterior horn cells of the spinal cord or brainstem nuclei.

Amyotrophic lateral (ALS) is sclerosis a rare degenerative neurological disease, the cause of which is unknown, and is also called "motor neuron disease" or "Lou Gehrig's disease" because motor neurons in the spinal cord are selectively destroyed. This is a chronic degenerative disease that causes death within a few years due to muscle weakness and muscular atrophy of the extremities, paralysis of the extremities, speech disorders, decreased respiratory function and the like.

Spinal bulbar muscular atrophy (SBMA), which is also called "Kennedy's disease", is a genetic disorder in which loss of motor neurons, i.e., loss of neurons in the spinal cord and brainstem, affects the part of the nervous system that controls voluntary muscle movement. SBMA is an X chromosome genetic disease which mainly affects men and causes hormonal dysfunction related to loss of testosterone functions. SBMA also mainly affects the muscles of the face, muscles involved in swallowing, and the muscles of the arms and legs, especially the muscles closest to the center of the body.

Duchenne muscular dystrophy (DMD) is the most common muscular dystrophy in children. The first symptoms usually appear between the ages of 2 and 6 years. Early symptoms include frequent falls and difficulty sitting up, waddling, and enlarged calf muscles. Duchenne muscular atrophy is an X chromosome-linked recessive disorder found mainly in boys, and the muscles of the buttocks, upper arms, and thighs are damaged first. In some cases, Duchenne muscular atrophy is accompanied by mild mental retardation. Duchenne muscular dystrophy progresses slowly, but a child at the age of 12 may need a wheelchair. In a later stage, breathing difficulty occurs and antibiotics and respiration therapy may be required. In the final stage, children may have severe breathing and heart problems, most of which occur in their teens or early twenties. Duchenne muscular atrophy patients may also receive gene therapy.

Becker muscular dystrophy (BMD) has similar onset and symptoms to those of Duchenne muscular dystrophy, but the onset thereof is later and the progression thereof is slow compared to Duchenne muscular dystrophy. The two types of muscular atrophy described above are attributable to damage to the same genes, but the damage is different. Becker muscular atrophy can also be treated with gene therapy. Becker muscular dystrophy is an X chromosome-linked recessive disorder most commonly found in males. Becker muscular dystrophy is characterized in that the muscles of the upper arms, thigh, and buttocks are damaged first, the onset period is 2 to 16 years old, and walking is possible into the patient's 30s.

Stroke (cerebral ischemia) is a condition in which edema of the surrounding brain tissue and ischemia of brain cells occur due to circulatory disorders in the brain, leading to local or general sudden neurological deficits, resulting in movement disorders, sensory disorders, cognitive disorders, and speech disorders. Stroke causes muscular atrophy due to decreased activity or movement attributable to hemiplegia, decreased blood supply, decreased nutritional intake, decreased hormone stimulation, and decreased nerve stimulation.

Facioscapulohumeral muscular dystrophy (FSH) is an autosomal dominant muscular atrophy that affects both boys and girls, and first appears in adolescence or early adulthood. The initial symptoms include shoulders bent forward, difficulty raising the arms above the head, difficulty closing the eyes, and gradual progression of muscle weakness to the abdominal muscles, feet, upper extremities, and buttocks. Symptoms vary in severity and progress slowly. About half of FSH patients may be able to walk continuously.

As used herein, the term "prevention" refers to any action that suppresses or delays the onset of muscular atrophy or sarcopenia by administration of the pharmaceutical composition according to the present invention.

As used herein, the term "treatment" refers to any action that ameliorates or beneficially changes symptoms due to muscular atrophy or sarcopenia by administration of the pharmaceutical composition according to the present invention.

The composition of the present invention may further contain one or more active ingredients exhibiting the same or similar function in addition to 2'-FL.

The pharmaceutical composition of the present invention may further contain a pharmaceutically acceptable carrier in addition to 2'-FL.

The type of carrier that can be used in the present invention is not particularly limited and any carrier commonly used in the art may be used. Non-limiting examples of the carrier include lactose, dextrose, sucrose, sorbitol, mannitol, saline, sterile water, Ringer's solution, buffered saline, albumin injection solution, xylitol, erythritol, maltitol, maltodextrin, glycerol, ethanol, and the like. These may be used alone or in combination of two or more thereof.

In addition, the pharmaceutical composition of the present invention may further contain other pharmaceutically acceptable additives such as antioxidants, excipients, diluents, buffers or bacteriostats, if necessary, and may further contain surfactants, binders, fillers, extenders, wetting agents, disintegrants, dispersants or lubricants.

The 2'-FL may be contained in the pharmaceutical composition of the present invention in an amount of 0.00001 wt % to 99.99 wt %, preferably 0.1 wt % to 90 wt %, more preferably 0.1 wt % to 70 wt %, even more preferably 0.1 wt % to 50 wt %, based on the total weight of the pharmaceutical composition, but is not limited thereto, and the content of the 2'-FL may vary depending on the condition of the subject to which the composition is administered, the type of specific disease, the degree of progression of the disease, and the like. If necessary, 2'-FL may be present in an amount equal to the total amount of the pharmaceutical composition.

That is, the pharmaceutically effective amount and effective dosage of the pharmaceutical composition of the present invention may vary depending on the formulation method, administration method, administration time, and/or route of administration of the pharmaceutical composition, and may vary depending on several factors including the type and extent of the reaction that is achieved by administration of the pharmaceutical composition, the type, age, weight, general health condition, symptoms or severity of disease, gender, diet and excretion, of the subject to which the composition is administered, and the ingredients of drug or other composition administered simultaneously or sequentially to the subject, and the like, and similar factors well known in the pharmaceutical field. Those skilled in the art can easily determine and prescribe an effective dosage for the desired treatment. For example, the daily dose of the pharmaceutical composition of the present invention is about 0.01 to 1,000 mg/kg, preferably 0.1 to 100 mg/kg, and may be administered once a day or several times a day, divided into multiple doses.

The pharmaceutical composition of the present invention may be administered once a day or several times a day, divided into multiple doses. The pharmaceutical composition of the present invention may be administered as a single therapeutic agent or in combination with other therapeutic agents, sequentially or simultaneously with conventional therapeutic agents. Taking into consideration these factors, it is important to administer the composition in the minimum amount sufficient to achieve maximum efficacy without side effects, which can be easily determined by those skilled in the art.

The pharmaceutical composition of the present invention may be used in combination with various methods such as hormone therapy and drug therapy to prevent or treat muscular atrophy or sarcopenia.

As used herein, the term "administration" means supplying the pharmaceutical composition of the present invention to a patient using any suitable method. The route and mode of administration of the pharmaceutical composition of the present invention may be independent and any route and mode of administration may be used without particular limitation as long as the pharmaceutical composition can reach the desired site.

The pharmaceutical composition may be administered in an oral or parenteral administration mode, and may be prepared and used in various formulations suitable for oral administration or parenteral administration.

Non-limiting examples of formulations for oral administration using the pharmaceutical composition of the present invention include oily suspensions, troches, lozenges, tablets, aqueous suspensions, prepared powders, granules, emulsions, hard capsules, soft capsules, syrups, elixirs, or the like.

In order to formulate the pharmaceutical composition of the present invention for oral administration, a binder such as sorbitol, mannitol, starch, amylopectin, cellulose, lactose, saccharose or gelatin, a lubricant such as magnesium stearate, calcium stearate, sodium stearyl fumarate or polyethylene glycol wax, an excipient such as dicalcium phosphate, a disintegrant such as corn starch or sweet potato starch, a fragrance, syrup, sweetener or the like may be used. Furthermore, in the case of capsules, in addition to the above-mentioned substances, a liquid carrier such as fatty oil may be further used.

The parenteral administration of the pharmaceutical composition of the present invention may be carried out by intramuscular administration, transdermal administration, intravenous administration, intraperitoneal administration, or subcutaneous administration, and the composition may be applied, sprayed, or inhaled to a diseased site, but the parenteral administration is not limited thereto.

Non-limiting examples of parenteral preparations using the pharmaceutical composition of the present invention include injections, suppositories, ointments, powders for application, oils, powders for respiratory inhalation, aerosols for sprays, creams, and the like.

In order to formulate the pharmaceutical composition of the present invention for parenteral administration, sterile aqueous solutions, non-aqueous solvents, suspensions, emulsions, lyophilizates, external preparations, and the like may be used. The non-aqueous solvents and suspensions may include vegetable oils such as olive oil, injectable esters such as propylene glycol, polyethylene glycol, ethyl oleate and the like.

When the pharmaceutical composition of the present invention is formulated as an injection solution, it is obtained by mixing the pharmaceutical composition with a stabilizer or buffer in the presence of water to prepare a solution or suspension and injecting the solution or suspension into a unit container such as an ampoule or vial.

When the pharmaceutical composition of the present invention is formulated as an aerosol, a propellant or the like may be blended with an additive so as to disperse the water-dispersed concentrate or wet powder.

When the pharmaceutical composition of the present invention is formulated as an ointment, oil, cream, powder for application, external preparation for skin, or the like, an animal oil, vegetable oil, wax, paraffin, polyethylene glycol, silicone, bentonite, silica, talc, starch, tragacanth, cellulose derivatives, or zinc oxide may be used as the carrier ingredient.

Meanwhile, the present invention provides a food composition for ameliorating muscular atrophy or sarcopenia or strengthening muscles containing 2'-FL as an active ingredient.

The content of 2'-FL in the food composition of the present invention is not particularly limited and may vary depending on the condition of the subject to which the composition is administered, the type of specific disease, the degree of progression of the disease, and the like. If necessary, the content of 2'-FL may be equal to the total content of the food.

The food composition of the present invention may be, for example, any one selected from noodles, gums, dairy products, ice cream, meat, grains, caffeinated beverages, general drinks, chocolate, bread, snacks, confectionery, candy, pizza, jellies, alcoholic beverages, alcohol, vitamin complexes and other health supplements, but is not limited thereto.

When the food composition of the present invention is used in the form of a food additive, it may be added alone or used in combination with other food or food ingredients, and may be appropriately used according to a conventional method.

In addition, the food composition of the present invention includes health functional food. The term "health functional food" means food manufactured and processed using raw materials or ingredients useful for the human body, and the term "functional" means intake of food with the goal of obtaining beneficial effects for health such as regulation of nutrients appropriate for structures and functions of the human body or physiological effects.

The food composition of the present invention may contain additional ingredients that are commonly used to improve odor, taste, vision, and the like. For example, the food composition may contain biotin, folate, pantothenic acid, vitamins A, C, D, E, B1, B2, B6, and B12, niacin, and the like. For example, the food composition may contain minerals such as chromium (Cr), magnesium (Mg), manganese (Mn), copper (Cu), zinc (Zn), iron (Fe), and calcium (Ca). In addition, the food composition may contain amino acids such as cysteine, valine, lysine, and tryptophan. In addition, the food composition may contain food additives such as preservatives (such as potassium sorbate, sodium benzoate, salicylic acid, and sodium dehydroacetate), coloring agents (such as tar pigments), coloring agents (such as sodium nitrite and sodium nitrite), bleach (sodium sulfite), disinfectants (such as bleaching powder and high-grade bleaching powder, and sodium hypochlorite), expanders (such as alum, D-potassium hydrogen tartrate), reinforcements, emulsifiers, thickeners, coating agents, antioxidants (such as butylhydroxyanisole (BHA), and butylhydroxytoluene (BHT), seasonings (such as MSG), sweeteners (such as dulcin, cyclamate, saccharin, and sodium), flavorings (such as vanillin and lactones), gum bases, foam inhibitors, solvents, enhancers, and the like. The food additives may be selected depending on the type of food and used in an appropriate amount.

Hereinafter, the present invention will be described in more detail with reference to the following examples and experimental examples. The scope of the present invention is not limited to the examples and experimental examples, and encompasses modifications of the technical concept equivalent thereto.

Example 1: Evaluation of Muscle Strengthening Efficacy of 2'-FL Using C2C12 Cell Line 1. C2C12 Culture and MTT Assay C2C12, a mouse muscle (myoblast) cell line, was cultured at 37° C. in the presence of 5% $CO_2$ using a medium containing 90% DMEM, 10% FBS, and 10 unit/ml penicillin-streptomycin.

In order to confirm the cytotoxicity of 2'-FL, the C2C12 cell line was seeded in each well of a 96-well plate at a concentration of $5 \times 10^4$ cells/well, cultured for 24 hours, and then treated with 2'-FL at various concentrations (100, 200, 400 μM) for 24 hours. Then, the medium was removed and a growth medium and 0.5 mg/ml of a diluted MTT solution were aliquoted in an amount of 2 mL and incubated in a $CO_2$ incubator. After 2 hours, the MTT reagent was removed, formazin was dissolved in DMSO (dimethyl sulfoxide), and absorbance was measured at 540 nm.

The result of the experiment showed that there was no difference in cell viability between any one of all groups treated with 2'-FL at all concentrations (100, 200, 400 μM) and the control group (FIG. 1). FIG. 1 shows cell viability after treatment with 2'-FL.

2. MHC Expression Analysis Using Immunocytochemical Staining

In order to differentiate mouse myoblasts into myotubes, the mouse myoblasts were seeded at a concentration of $4 \times 10^5$ cells/well in each well of a 6-well plate, cultured for 24 hours until confluence reached 100% and then 2% horse serum was added thereto. Then, the mouse myoblasts were differentiated for 6 days while exchanging the DMEM containing 2% horse serum with fresh DMEM every 2 days.

Immunocytochemical staining was performed to determine the effect of treatment with 2'-FL on myocyte differentiation. Specifically, C2C12 was treated with 2'-FL at different concentrations (100 and 200 μM) for 24 hours, and then fixed with a 4% paraformaldehyde solution for 10 minutes. The fixed cells were washed with PBS containing 0.1% Triton X-100 and then reacted in 5% BSA solution for 1 hour. The cells were washed 3 times with 1×PBS again and then were allowed to react with an MHC antibody (Cell signaling) at room temperature overnight.

After the reaction was completed, the cells were washed 3 times with PBS and reacted with Alexa Fluor 488 goat anti-rabbit IgG at room temperature for 1 hour, and then nuclei thereof were stained with a horchest solution and observed under a fluorescence microscope. At this time, the AMPK agonist A-769662 (1 μM) was used as a positive control.

Figure 2:
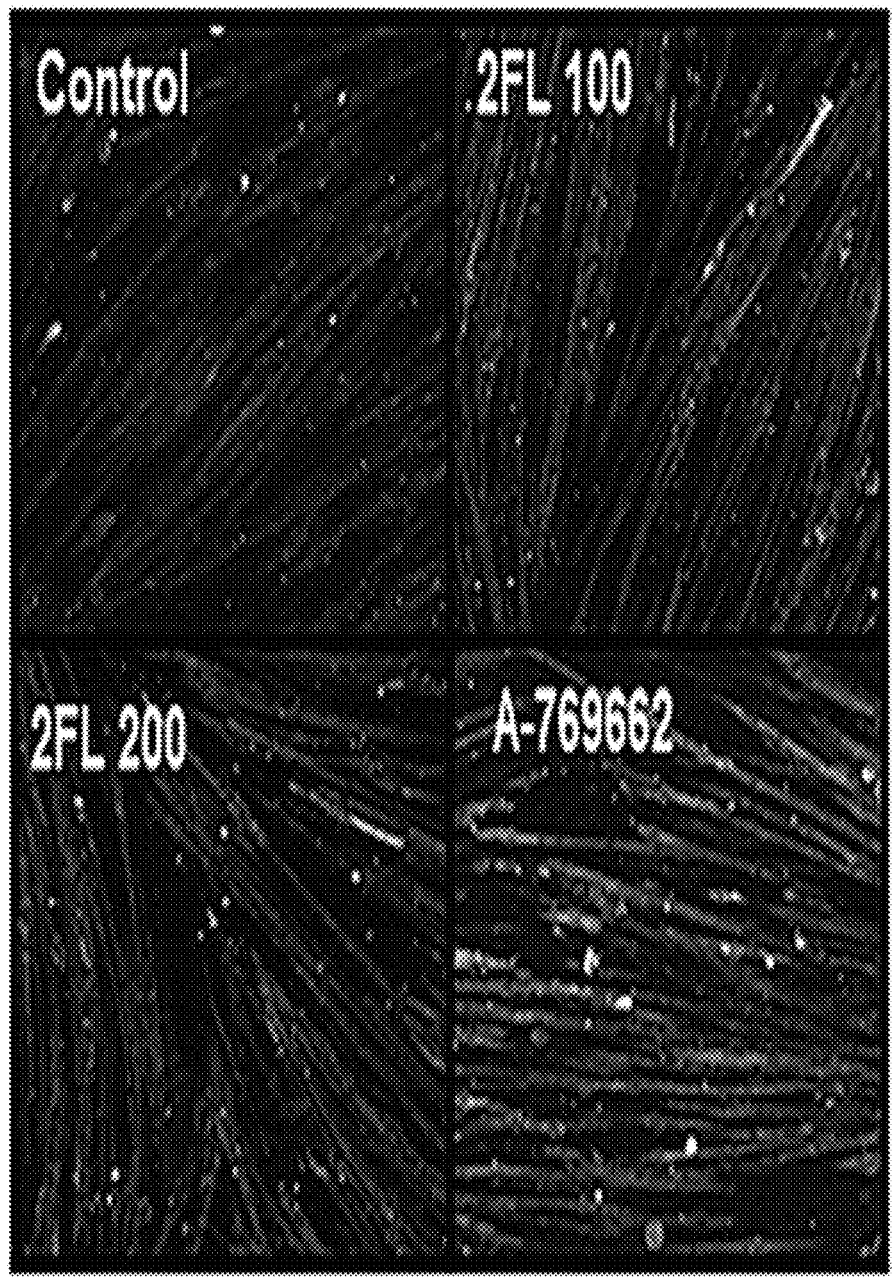
FIG. 2 shows the effect of controlling muscle differentiation, obtained by treatment with 2'-FL.

The result of the experiment showed that both the MHC expression and the length and thickness of myotubes increased in the groups treated with 2'-FL compared to the control group (FIG. 2). FIG. 2 shows the muscle differentiation control efficacy obtained by treatment with 2'-FL.

Therefore, it was found that 2'-FL increased muscle differentiation in the C2C12 cell line.

3. Evaluation of the Efficacy of Enhancing Mitochondrial Function

Mitochondria have mitochondrial DNA (mtDNA) that is isolated from their own nuclear DNA. Unlike nuclear DNA of cells, mtDNA does not have a repair mechanism to repair damage and a histone protein to protect DNA, thus being relatively readily damaged. Such damage to mtDNA causes a decrease in mitochondrial function, leading to a decrease in synthesis of ATP, which is an energy molecule required for cellular a decrease in the ability to regulate activity, and homeostasis in vivo, which eventually causes the onset of various diseases. Accordingly, mtDNA expression and mitochondrial density upon treatment with 2'-FL were measured.

For this purpose, the change in mitochondrial density after treatment of C2C12, which has been differentiated, with 2'-FL was observed with MitoTracker. C2C12 was treated with 2'-FL at different concentrations (100 and 200 μM) for 24 hours, was washed with PBS, added with a medium containing 200 nM of a MitoTracker green probe and cultured for 30 minutes. Then, the portion bound to the MitoTracker green probe was quantified with SpectraMax that absorbs a wavelength of 490 nm and emits a wavelength of 516 nm to measure the density of mitochondria. At this time, the AMPK agonist A-769662 (1 μM) was used as a positive control.

Figure 3:
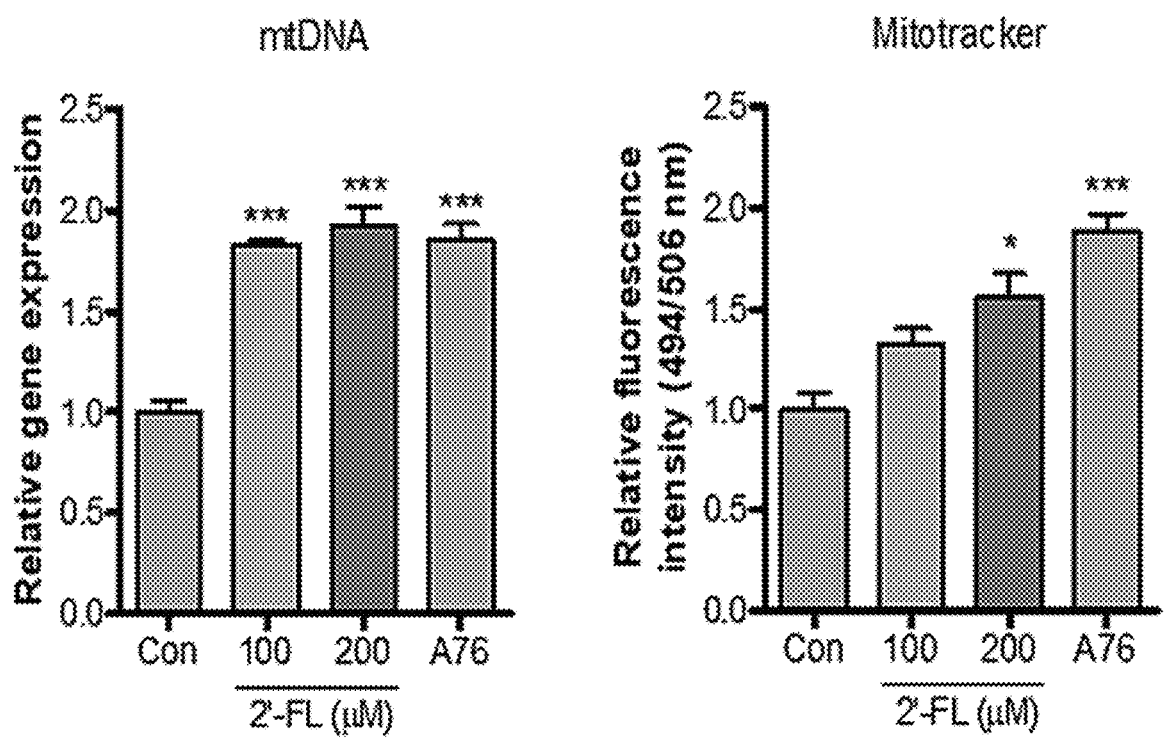
FIG. 3 shows the effect of enhancing mitochondrial functions, obtained by treatment with 2'-FL.

The result of the experiment showed that mtDNA expression was significantly increased in a concentration-dependent manner in the group treated with 2'-FL compared to the control group, and the mitochondrial density measured using the MitoTracker was also increased in a concentration-dependent manner in the group treated with 2'-FL compared to the control group (FIG. 3). FIG. 3 shows the effect of enhancing mitochondrial functions, obtained by treatment with 2'-FL. These results show that 2'-FL regulates mitochondrial functions.

4. Confirmation of Gene Expression Changes Related to Mitochondrial Biosynthesis Mitochondria are organelles that have a main function of generating ATP, which is a form of intracellular energy, and perform various intracellular functions such as metabolism, signal transduction, apoptosis, and differentiation. Metabolic adaptation in skeletal muscle is achieved by the regulation of various genes, and PGC-1α (peroxisome proliferator-activated receptor-γ coactivator-1α) transcriptional cofactor is known to perform the most important role therefor. Accordingly, the mRNA expression changes of PGC-1α and the downstream gene thereof, NRF2, were determined upon treatment with 2'-FL.

For this purpose, CDNA was synthesized from RNA extracted from C2C12 cells using ReverTra Ace qPCR RT Kit (TOYOBO). In order to increase the efficiency of the reaction, the RNA was pre-heated at 65° C. for 5 minutes and then immediately stored on ice. Then, a total of 8 μl of reagent was prepared from 2 μl of 4×DN master mix containing a gDNA remover, 0.5 μg of mRNA, and nuclease-free water, and then was amplified at 37° C. for 5 minutes.

The reacted reagent was added with a 5×RT master mix, and amplified at 37° C. for 15 minutes, at 50° C. for 5 minutes, and at 98° C. for 5 minutes to synthesize cDNA. Then, the synthesized cDNA was subjected to qPCR using Thunderbird TMSYBR qPCR mix reagent (TOYOBO). The gene expression level was analyzed with the iQ5 Cycler System (Bio-Rad). In this case, the AMPK agonist A-769662 (1 μM) was used as a positive control.

Figure 4:
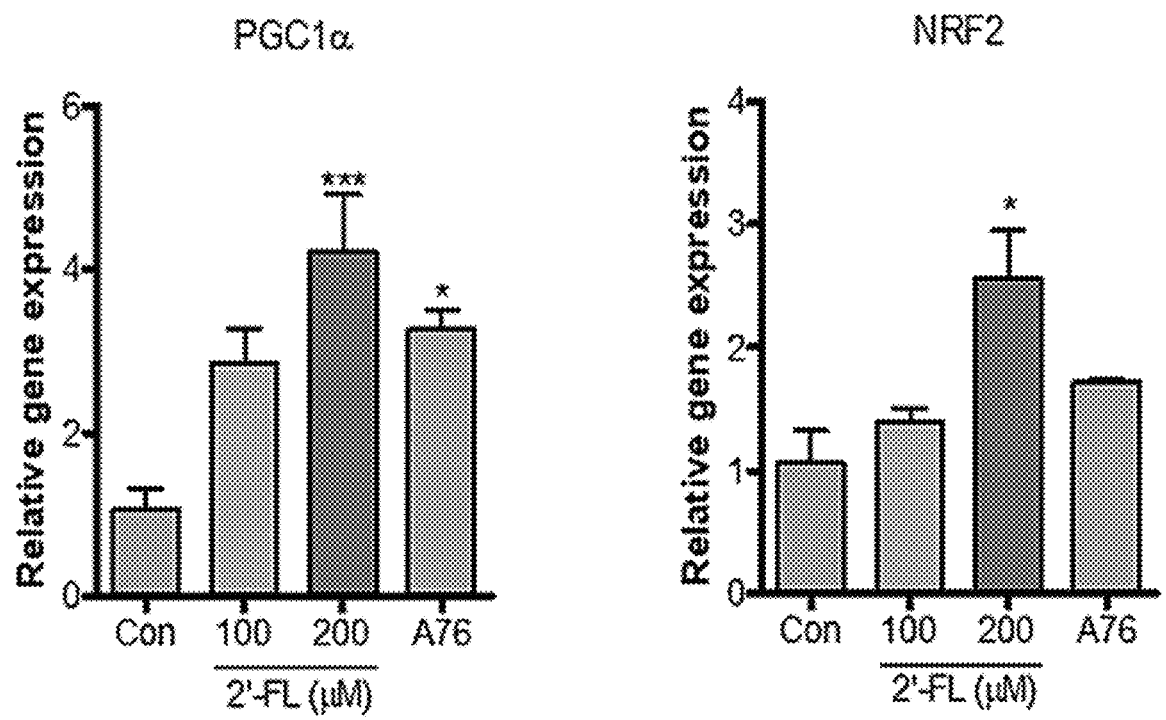
FIG. 4 shows mRNA expression changes of PGC-1α and the downstream gene NRF2 upon treatment with 2'-FL.

The result of the experiment showed that the expression of PGC-1α and NRF2 mRNA was significantly increased in the group treated with 2'-FL at a high concentration compared to the control group (FIG. 4). FIG. 4 shows mRNA expression changes of PGC-1α and the downstream gene NRF2 upon treatment with 2'-FL.

Overall, it can be seen from the above results that 2'-FL facilitates the differentiation of C2C12 myoblasts into myotubes, and increases mtDNA expression and mitochondrial density, thereby improving mitochondrial function. In addition, it can be seen that 2'-FL increases the expression of PGC-1α and NRF2 mRNA, which are e genes related to mitochondrial biosynthesis.

It can be seen from these results that treatment with 2'-FL is effective in strengthening muscles and whether or not 2'-FL can induce an effect of preventing muscular atrophy based on this effect will be determined in Example 2 below.

Example 2: Evaluation of Effect of Preventing Muscular Atrophy of 2'-FL Using C2C12 Cell Line Dexamethasone, a synthetic glucocorticoid, is known to decrease the rate of protein synthesis and increase the rate of protein degradation in muscles in vivo or in cultured cells. Accordingly, 1 hour after treatment of C2C12, which had been differentiated, with 2'-FL, C2C12 was treated with dexamethasone at a concentration of 400 µM for 24 hours to determine the muscular atrophy prevention effect of 2'-FL in a cell model.

1. Evaluation of Protection of Growth Inhibition and Differentiation Inhibition Caused by Treatment with Dexamethasone In order to evaluate the prophylactic effect of growth inhibition caused by treatment with dexamethasone, C2C12 was treated with 2'-FL and dexamethasone in the same manner as above, the cells were removed with trypsin, and the number of the cells was counted using trypan blue staining.

Meanwhile, in order to evaluate the prophylactic effect of the differentiation inhibition caused by treatment with dexamethasone, the length and diameter of myotubes were measured after treatment with dexamethasone.

The result of the experiment showed that the number of cells was significantly decreased in a group treated with dexamethasone (Veh) compared to an experimental group not treated with dexamethasone (Nor), whereas the number of cells was significantly increased in a group treated with 2'-FL at a high concentration (200 µM) compared to a group treated with dexamethasone (Veh).

Figure 5:
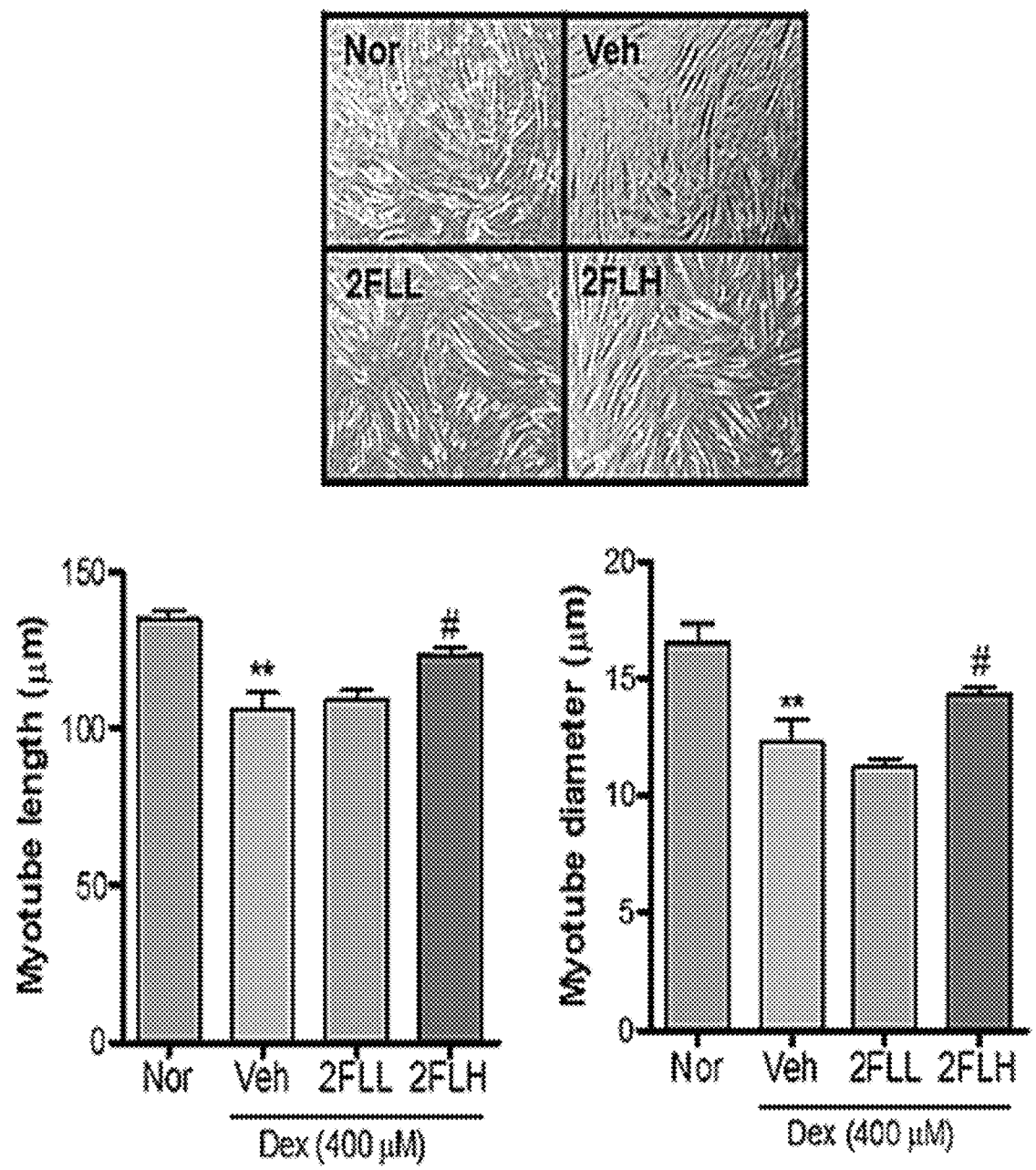
FIG. 5 shows the prophylactic effect of treatment with 2'-FL against muscular atrophy induced by treatment with dexamethasone.

In addition, it can be seen that the length and diameter of myotubes were significantly decreased in the group treated with dexamethasone (Veh) compared to the experimental group not treated with dexamethasone (Nor), whereas the length and diameter of myotubes were significantly increased in the group treated with 2'-FL at a high concentration (200 µM) compared to the group treated with dexamethasone (Veh). FIG. 5 shows the prophylactic effect of treatment with 2'-FL against muscular atrophy induced by treatment with dexamethasone. In FIG. 5, 2FLL represents a group treated with 2'-FL at 100 µM, and 2FLH represent a group treated with 2'-FL at 200 µM.

Figure 6:
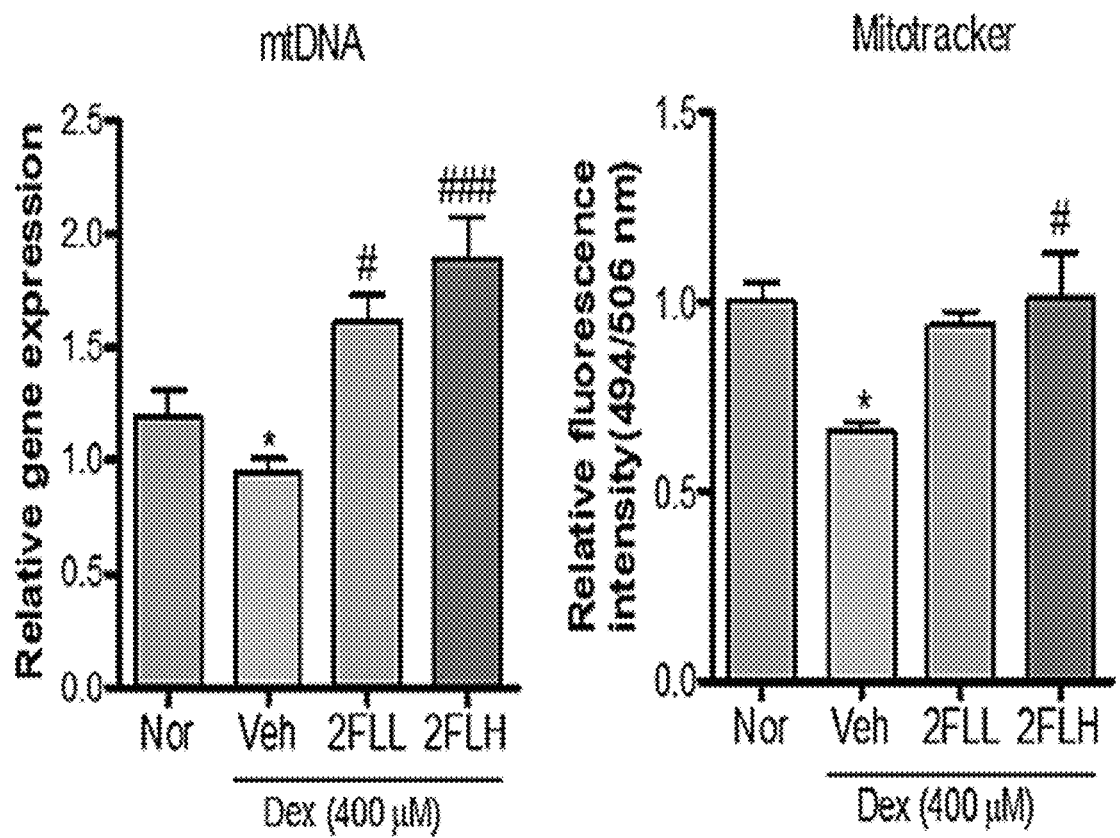
FIG. 6 shows the prophylactic effect of treatment with 2'-FL against mitochondrial function inhibition induced by treatment with dexamethasone.

2. Evaluation of Prophylactic Effect Against Mitochondrial Function Inhibition Caused by Dexamethasone Treatment After treatment with dexamethasone, mtDNA expression and mitochondrial density were measured. The result of the experiment showed that significant mtDNA expression and mitochondrial density were decreased in the group treated with dexamethasone (Veh) compared to the group not treated with dexamethasone (Nor), whereas the mitochondrial function was significantly increased in the group treated with 2'-FL (Veh), compared to the group treated with dexamethasone (FIG. 6). FIG. 6 shows a prophylactic effect of 2'-FL treatment against mitochondrial function inhibition induced by treatment with dexamethasone. In FIG. 6, 2FLL represents a group treated with 2'-FL at 100 µM, and 2FLH represent a group treated with 2'-FL at 200 µM.

3. Changes in Gene Expression Related to Muscular Atrophy

Muscular atrophy relates to two muscle-specific E3 ubiquitin ligases, that is, MAFbx (muscular atrophy F-box)/atrogin-1 and MuRF1 (muscle RING finger-1). Dexamethasone has been reported to reduce muscle mass by decomposing muscular proteins through these ligases and reducing myogenin and MyoD (myogenic differentiation antigen), which are muscle-specific factors involved in muscle differentiation. Accordingly, an experiment was conducted to determine whether or not 2'-FL increased the expression of genes related to muscular atrophy, which was decreased by dexamethasone treatment. The experiment was performed in the same manner as No. 4 of Example 1 except that the antibody was changed.

Figure 7:
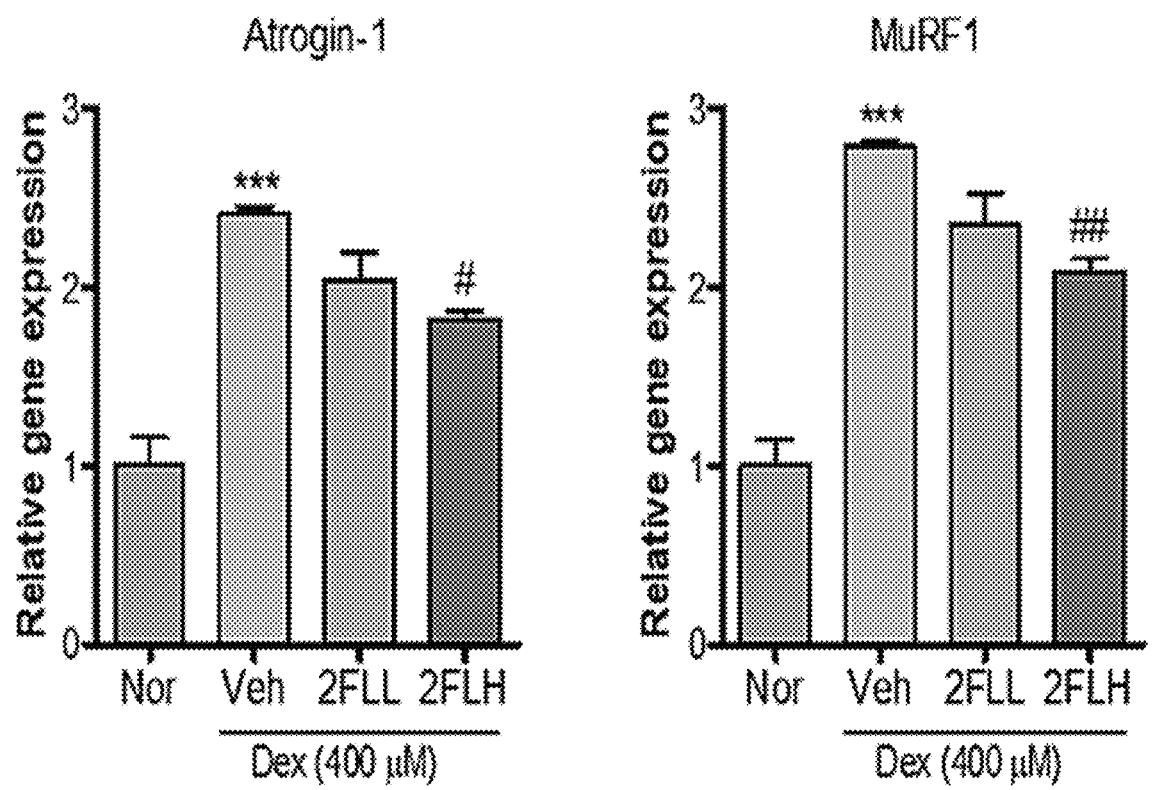
FIG. 7 shows expression changes of atrogin-1 and MuRF1 genes upon treatment with 2'-FL.

The result of the experiment showed that atrogin-1 and MuRF1 gene expression were significantly increased in the group treated with dexamethasone (Veh) compared to the group not treated with dexamethasone (Nor), and that atrogin-1 and MuRF1 gene expression were significantly decreased compared to the group treated with dexamethasone (Veh) upon treatment with 2'-FL (FIG. 7). FIG. 7 shows expression changes of atrogin-1 and MuRF1 genes upon treatment with 2'-FL. In FIG. 7, 2FLL represents a group treated with 2'-FL at 100 µM, and 2FLH represent a group treated with 2'-FL at 200 µM.

Overall, it can be seen from the above results that 2'-FL has a prophylactic effect against reduction in cell number and mitochondrial function caused by dexamethasone treatment and was effective in preventing muscular atrophy by reducing the expression of atrogin-1 and MuRF1 genes, which are markers for muscular atrophy. Whether or not these results are the same in an animal model will be determined in Example 3 below.

Example 3: Evaluation of Muscular Atrophy Prophylactic Effect of 2'-FL Using Animal Model 1. Animal Experiment Design In order to determine whether or not 2'-FL has a prophylactic effect against muscular atrophy in an animal model, 2'-FL was orally administered at a concentration of 200 or 400 mg/kg to 7-week-old male C57BL/6 mice for 7 days, followed by intraperitoneal injection of dexamethasone known as a drug inducing muscular atrophy at a concentration of 10 mg/kg, and at the same time, oral administration of 2'-FL for 2 weeks.

At this time, the experiment was conducted on mouse experimental groups, namely, a Nor group that received intraperitoneal injection of saline and distilled water, a that received intraperitoneal injection of Veh group dexamethasone and was orally administered distilled water, and a 2FLL group and a 2FLH group that received intraperitoneal injection of dexamethasone and was orally administered 2'-FL at 200 mg/kg and 400 mg/kg, respectively.

Figure 8:
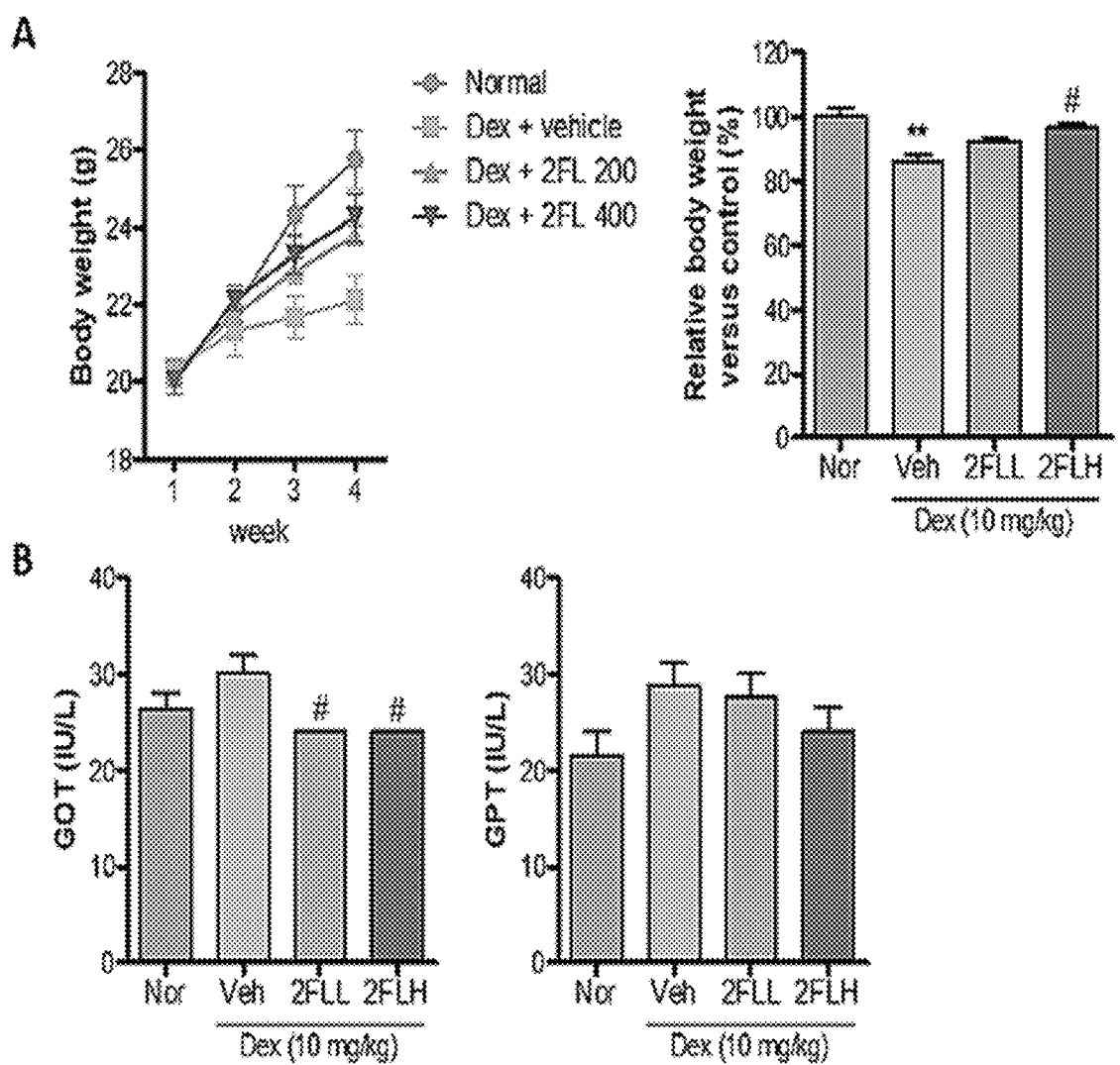
FIG. 8 shows the prophylactic effect of 2'-FL against body damage induced by treatment with dexamethasone in an animal model (A: results of measurement of weight of animal model for experimental groups, B: results of liver function test for experimental groups (GOT, GPT))

The result of the experiment showed that the mouse weight measured for 3 weeks of an animal experiment period was increased in the group treated with 2'-FL at a high concentration (2FLH) compared to the group treated with dexamethasone (Veh). In addition, the plasma liver function test (GOT, GPT) showed that the GOT and GPT activities were lowered in the group treated with 2'-FL compared to the group treated with dexamethasone (Veh) (FIG. 8). FIG. 8 shows a prophylactic effect of 2'-FL against body damage induced by treatment with dexamethasone in an animal model (A: results of measurement of weight of animal model for experimental groups, B: results of liver function test for experimental groups (GOT, GPT).

These results show that oral administration of 2'-FL prevents damage to the body upon intraperitoneal administration of dexamethasone.

2. Observation of Histological Morphology of Mouse Muscle Tissue

The mouse muscle tissue was stained using the H&E method and then histological morphology was observed.

The result of the experiment showed that the muscular atrophy morphological characteristics observed in the group treated with dexamethasone (Veh), such as decreased muscle bundle size and an imbalance in nuclear location, were ameliorated in the group treated with 2'-FL at a high concentration (2FLH).

Figure 9:
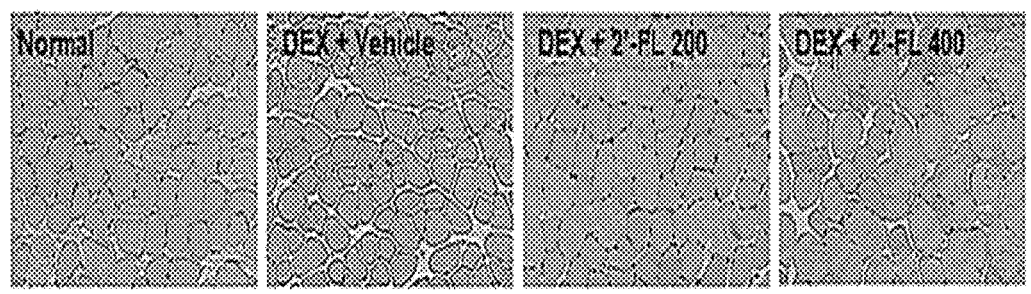
FIG. 9 shows the effect of 2'-FL on the amelioration of muscular atrophy induced by treatment with dexamethasone in an animal model (A: results of observation of histological morphology of muscle tissue, B: results of measurement of the weight of each muscle tissue (splenic muscle, gastrocnemius muscle, and extensor digitorum longus))
Figure 9:
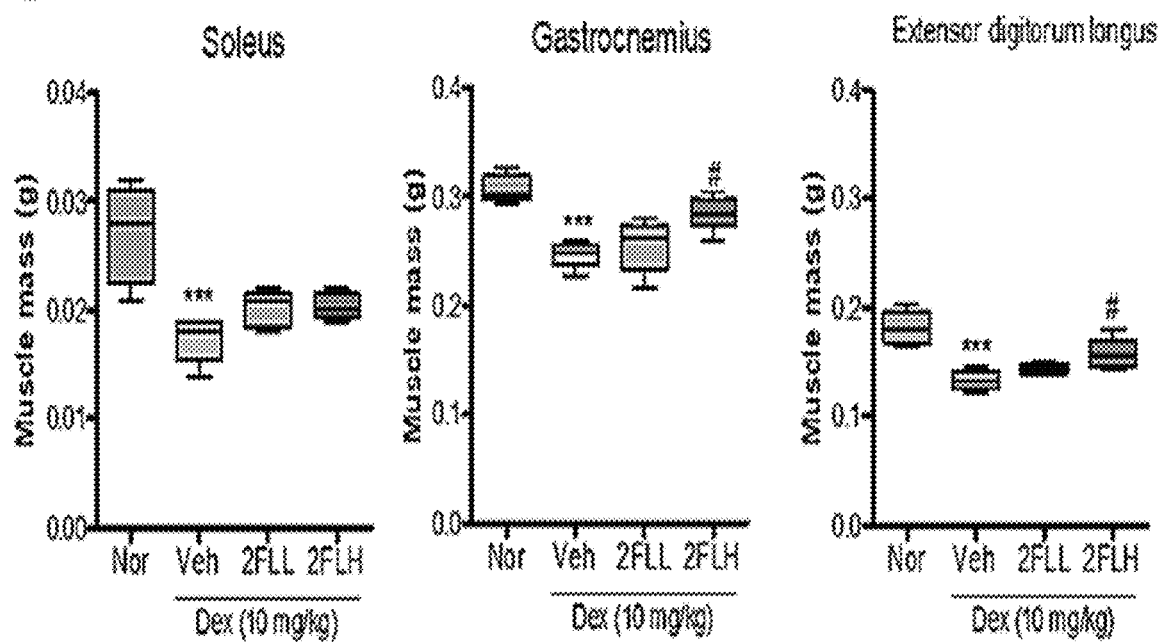

In addition, it can be seen that the weight of each muscle tissue (splenic muscle, gastrocnemius muscle, and extensor digitorum longus) was significantly increased in the group treated with 2'-FL at a high concentration (2FLH) compared to the group treated with dexamethasone (Veh) (FIG. 9). FIG. 9 shows the effect of treatment with 2'-FL on the amelioration of muscular atrophy induced by treatment with dexamethasone in an animal model (A: results of observation of histological morphology of muscle tissue, B: results of measurement of the weight of each muscle tissue (splenic muscle, gastrocnemius muscle, and extensor digitorum longus)).

3. Grip Strength Test

All experimental animals were subjected to a grip strength test using a grip strength meter (Jeongdo Bio & Plant Co., Ltd.) the day before the end of the experiment.

Figure 10:
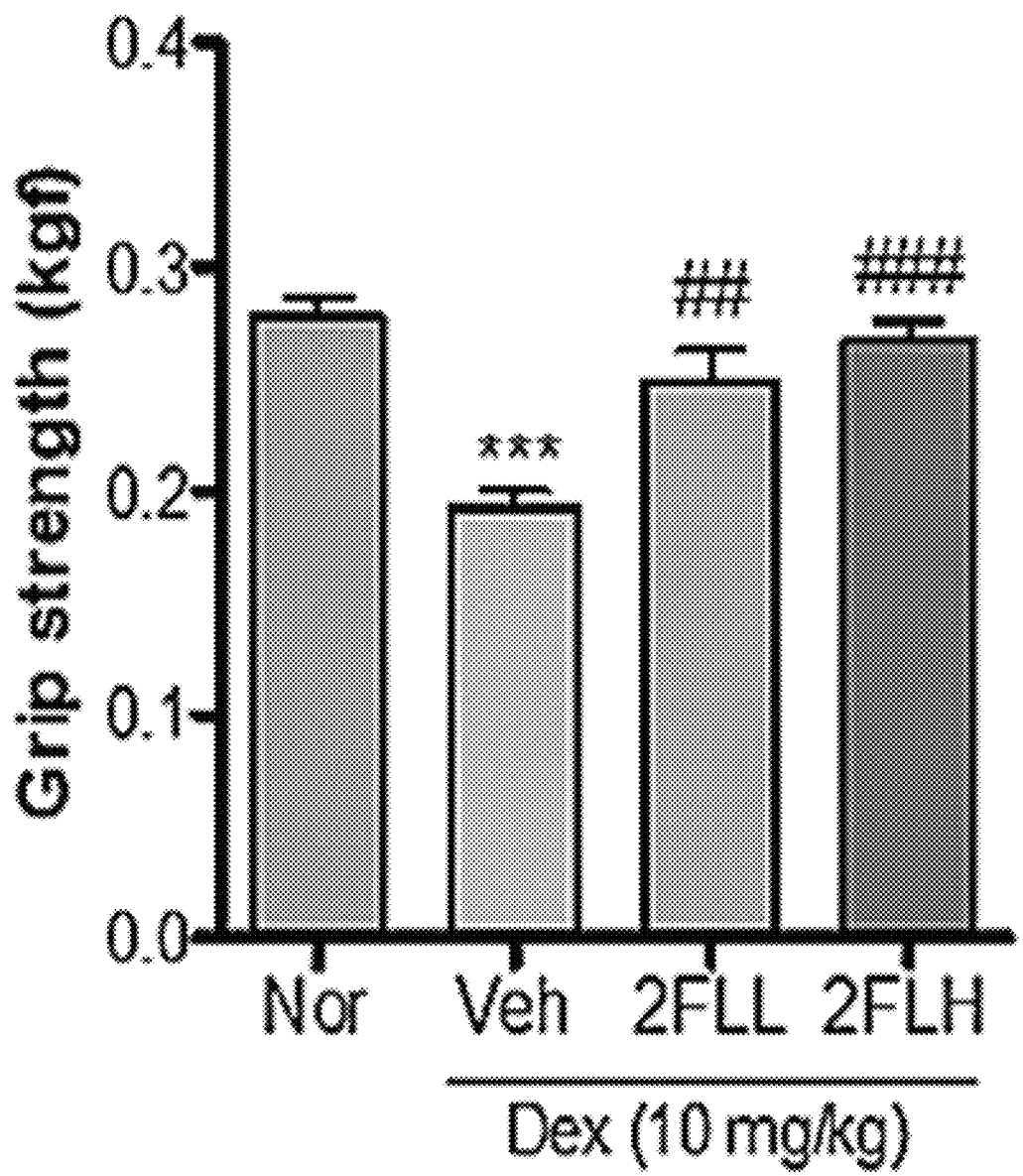
FIG. 10 shows the effect of treatment with 2'-FL on improvement in grip strength reduced by treatment with dexamethasone in an animal model.

The result of the experiment showed that the grip strength was significantly increased in the group treated with 2'-FL compared to the group treated with dexamethasone (Veh) (FIG. 10). FIG. 10 shows the effect of 2'-FL on improvement in grip strength reduced by treatment with dexamethasone in an animal model.

4. Confirmation of Protein Expression Related to Muscle Loss

Proteins were extracted by adding a Halt™ protease inhibitor to lysis buffer (10 mM Tris-HCl, pH 7.5, 1% NP-40, 0.1% sodium deoxycholate, 0.1% SDS, 150 mM NaCl, and 1 mM EDTA) in order to confirm protein expression using mouse muscle tissue and then immunoblotting was performed.

As primary antibodies, anti-α-tubulin (1:1000) and anti-atrogin-1 (1:1000) were used. The resulting image of immunoblotting was analyzed using a ChemiDoc™ touch imaging system (Bio-Rad) and Image Lab 5.2 software (Bio-Rad).

Figure 11:
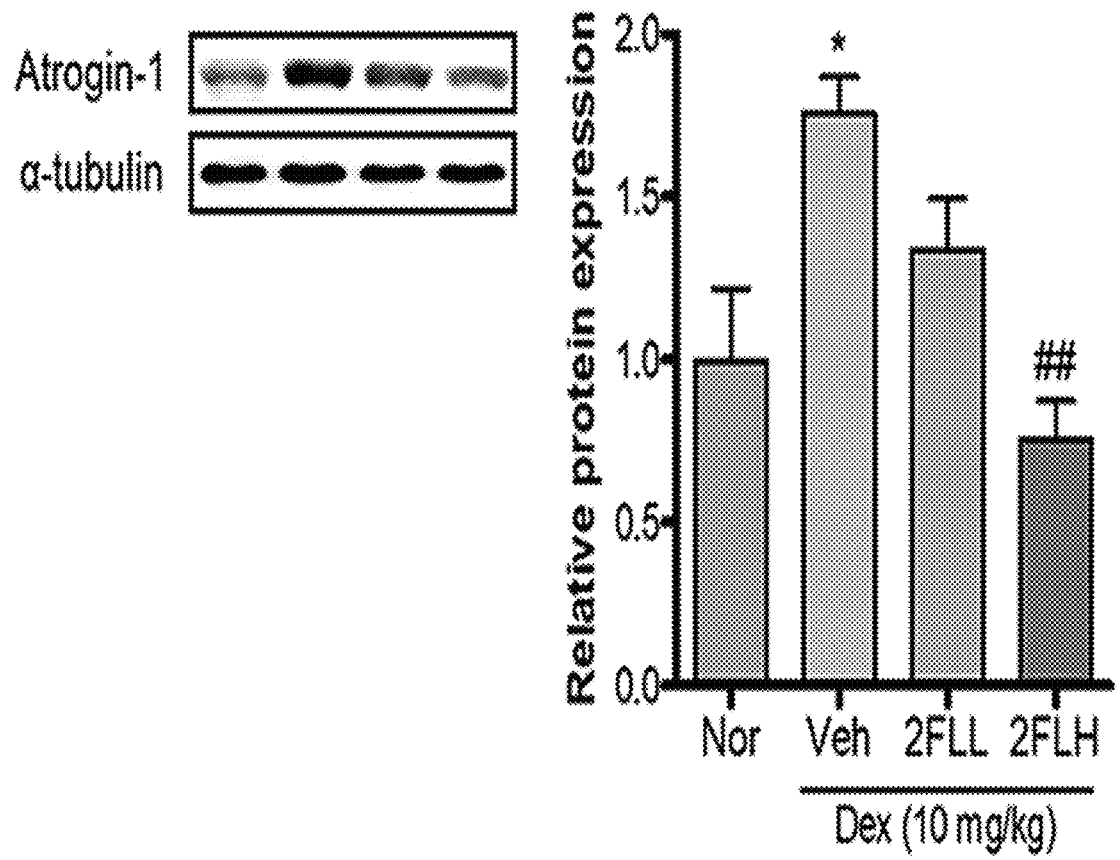
FIG. 11 shows the effect of 2'-FL on changes in atrogin-1 protein expression reduced by treatment with dexamethasone in an animal model.

The result of the experiment showed that the expression of atrogin-1 protein, a marker for muscular atrophy, was significantly decreased in the group treated with 2'-FL at a high concentration compared to the group treated with dexamethasone (Veh) (FIG. 11). FIG. 11 shows the effect of 2'-FL on changes in atrogin-1 protein expression reduced by treatment with dexamethasone in an animal model.

As is apparent from the foregoing, the composition for ameliorating, preventing or treating muscular atrophy or sarcopenia of the present invention increases the expression of genes related to mitochondrial function enhancement and mitochondrial biosynthesis, and reduces the expression of atrogin-1 and MuRF1 genes, which are markers for muscular atrophy, thereby providing effects of strengthening muscles and preventing muscular atrophy or sarcopenia.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for treating muscular atrophy, the method comprising administering a composition comprising 2'-fucosyllactose (2'-FL) as an active ingredient to a subject in need thereof,
    wherein the subject suffers from:
    (i) primary muscular atrophy which is induced by a lack of mechanical stimulation, decreased activity of neuromuscular junctions, decreased mitochondrial function, or nutritional deficiency, or
    (ii) secondary muscular atrophy which is induced by denervation due to stroke, excessive drug use, or changes in endocrine system hormones and sex hormones,
    wherein the subject requires increasing muscle differentiation or increasing a weight of muscle tissue, and
    wherein the 2'-fucosyllactose is administered at a dosage of 400 mg/kg/day based on a body weight of the subject.

2. The method according to claim 1, wherein the subject suffers from primary muscular atrophy which is induced by a lack of mechanical stimulation.

3. The method according to claim 1, wherein the subject suffers from primary muscular atrophy which is induced by decreased activity of neuromuscular junctions.

4. The method according to claim 1, wherein the subject suffers from primary muscular atrophy which is induced by decreased mitochondrial function.

5. The method according to claim 1, wherein the subject suffers from primary muscular atrophy which is induced by nutritional deficiency.

6. The method according to claim 1, wherein the subject suffers from secondary muscular atrophy which is induced by denervation due to stroke.

7. The method according to claim 1, wherein the subject suffers from secondary muscular atrophy which is induced by excessive drug use.

8. The method according to claim 1, wherein the subject suffers from secondary muscular atrophy which is induced by changes in endocrine system hormones.

9. The method according to claim 1, wherein the subject suffers from secondary muscular atrophy which is induced by sex hormones.

10. The method according to claim 1, wherein the subject requires increasing muscle differentiation and increasing a weight of muscle tissue.

* * * * *